United States Patent [19]
Gilbert et al.

[11] Patent Number: 5,122,449
[45] Date of Patent: Jun. 16, 1992

[54] USE OF A PROTEASE IN THE EXTRACTION OF CHLAMYDIAL, GONOCOCCAL AND HERPES ANTIGENS

[75] Inventors: James H. Gilbert, Oakland, Calif.; John C. Mauck, Rochester; Mark D. Stowers, Webster, both of N.Y.

[73] Assignee: Eastman Kodak Company, Rochester, N.Y.

[21] Appl. No.: 255,922

[22] Filed: Oct. 7, 1988

[51] Int. Cl.$^5$ .................... C12Q 1/00; C12Q 1/70; G01N 33/531

[52] U.S. Cl. ..................... 435/5; 435/7.36; 435/262; 435/267; 435/272; 436/17; 436/510

[58] Field of Search ............ 435/262, 267, 269, 272, 435/7, 5, 805, 810, 7.36; 436/510, 807, 17

[56] References Cited
U.S. PATENT DOCUMENTS

| | | | |
|---|---|---|---|
| 4,497,899 | 2/1985 | Armstrong et al. | 436/510 |
| 4,497,900 | 2/1985 | Abram et al. | 436/511 |
| 4,617,264 | 10/1986 | Whiteley et al. | 435/7.36 |
| 4,830,960 | 5/1989 | Appleton | 436/825 |
| 4,859,610 | 8/1989 | Maggio | 436/518 |
| 4,914,031 | 4/1990 | Zukowski et al. | 435/222 |

FOREIGN PATENT DOCUMENTS

| | | |
|---|---|---|
| 0131142 | 1/1985 | European Pat. Off. |
| 0174106 | 3/1986 | European Pat. Off. |
| 61-242596 | 10/1986 | Japan |
| 87/04461 | 7/1987 | World Int. Prop. O. |

OTHER PUBLICATIONS

Schmitt et al., "Surface-Exposed Antigenic Cleavage Fragments of *N. gonorrhoeae* Proteins IA and IB", *Infection & Immunology*, Dec. 1986, pp. 841-845, 1986.
Caldwell et al, *Infect. & Immun.*, 44(2); pp. 306-314 (1984).
Mearns et al, *J. Clin. Microbiol.*, 26 (2); pp. 1810-1813 (Sep. 1, 1988).
Stockman et al, *J. Clin. Microbiol.*, 16(5), pp. 965-967 (1982).

*Primary Examiner*—Sam Rosen
*Attorney, Agent, or Firm*—James L. Tucker

[57] ABSTRACT

An extraction method for lysing chlamydial, gonococcal or herpes organisms and extracting detectable antigen therefrom involves the use of a protease. In particular, the antigen can be effectively extracted from a biological specimen which contains whole blood or mucous using a protease. The extracted antigen can be effectively detected in an immunoassay involving antibodies directed to the antigen. The protease is novel to the process and is obtained from *Bacillus subtilisin*.

15 Claims, No Drawings

USE OF A PROTEASE IN THE EXTRACTION OF CHLAMYDIAL, GONOCOCCAL AND HERPES ANTIGENS

FIELD OF THE INVENTION

This invention relates to the use of a protease in the determination of chlamydial, gonococcal or herpes organisms. In particular, it relates to a method for the extraction of detectable antigens from those organisms which are in biological specimens also containing whole blood or mucous.

BACKGROUND OF THE INVENTION

Immunoassays have been used in recent years to detect the presence of infectious diseases. In order for the assay to be useful, it must detect a particular organism with a high degree of reliability. In most cases, this requires the isolation and reaction of antigens peculiar to the organism with corresponding antibodies. For the test to be commercially successful, it also needs to be relatively inexpensive, simple to use and rapid.

One such organism which can be detected by immunoassay is *Chlamydia trachomatis* (herein *C. trachomatis*) which is one of two microbial species of the genus Chlamydiaceae, order Chlamydiales. There are 15 or more strains of this species which are the causes of a number of human ocular and genital diseases including trachoma, inclusion conjunctivitis, lymphogranuloma venereum, nongonococcal urethritis and proctitis. Infection from *C. trachomatis* is pervasive in the general population so that it is believed that there are millions of cases each year of nongonococcal urethritis alone.

Despite the increasing control of various viruses by vaccination and various anti-viral agents, infection by organisms such as herpes simplex virus (HSV) remains a serious problem. There are two types of HSV, type 1 which occurs mainly around the mouth while type 2 occurs primarily around the genital area of the human body. Skin infections and viral encephalitis are but two of the serious results from HSV infection.

Gonorrhea is a disease usually transmitted by sexual contact caused by a bacterium of the Neisseria genus, especially *N. gonorrhoeae*. The disease has plagued mankind for thousands of years, and although antibiotics have helped control its spread, it still persists in epidemic proportions in many parts of the world. The importance of detection and treatment of this organism is well recognized. *N. meningitidis* and *N. lactamica* are also species of considerable medical and diagnostic interest.

Because of the widespread nature of these diseases, there is considerable interest in having a rapid, simple and reliable test for detection of chlamydial, gonococcal and herpes organisms. Considerable research has been carried out to find useful ways to extract detectable antigen from the organism. See for example, U.S. Pat. Nos. 4,427,782 (issued Jan. 24, 1984 to Caldwell et al) and 4,663,291 (issued May 5, 1987 to Rose) and E.P. Publications 174,106 (Becton) and 193,431 (Caldwell et al) which describe methods for extracting chlamydial antigens.

Extraction of antigen from the organisms in a biological specimen is critical to providing an accurate, rapid and sensitive assay. Many varied techniques have been used for extraction including physical disruption of the cells by sonication, heating or centrifugation. Chemical extraction compositions have also been developed. For example, the lipopolysaccharide antigen of *C. trachomatis* has been extracted using a mixture of phenol and water in E.P. Publication 193,431 (noted above).

Ethanolamine has been used in combination with surfactants and high temperature heating (for example, 70°-110° C.) to extract Chlamydial antigens as described in E.P. Publication 183,383 (IQ BIO). Extraction using high pH and heating is described in E.P. Publication 174,106 (noted above).

Assays for *C. trachomatis* and *N. gonorrhoeae* carried out using a solid support are described in U.S. Pat. Nos. 4,497,899 and 4,497,900 (both issued Feb. 5, 1985 to Armstrong et al and Abram et al, respectively). The described assays are performed by extracting antigen from the organism using a combination of an anionic or nonionic surfactant, deoxycholate and dithiothreitol, and coating it on a bare solid support. The coated antigen is then detected with either one or two antibodies, one of which is suitably labeled. Attachment of antigen is apparently achieved by incubating the coated support for an extended time sufficient to cause adsorption of antigen thereon (Col. 2, lines 51-55). From the examples of the patent, this time is determined to be at least 30 minutes at elevated temperature (37° C.). For example, the assay described in U.S. Pat. No. 4,497,899 takes at least 3 hours to perform.

A significant advance in the art is described in copending U.S. Ser. No. 255,928, filed Oct. 7, 1988 by Pronovost, Mauck, Sullivan, Greer and Gilbert, and entitled "High pH Extraction Composition and Its Use to Determine a Chlamydial, Gonococcal or Herpes Antigen". The invention claimed and described therein provides a rapid and effective means for extracting chlamydial, gonococcal or herpes antigens without resort to extended heating. Rather, a pH above about 8 and an ethanolamine are used for effective antigen extraction.

Despite the important advance provided by the invention just described, whole blood or mucous is sometimes present in biological specimens and acts to interfere with antigen extraction. Moreover, the presence of blood or mucous often reduces the sensitivity of the assay even if the extraction of antigen is rapid and efficient. The extraction techniques described above do not effectively overcome the problems caused by the presence of blood or mucous in the specimen.

It would be desirable to have a much more rapid test for chlamydial, gonococcal or herpes organisms which has high reliability and can be performed at room temperature. It would also be desirable to efficiently extract antigen and provide an efficient assay thereof even if whole blood or mucous is present in the specimen.

SUMMARY OF THE INVENTION

The problems noted above are overcome with a method for extracting antigen from chlamydial, gonococcal or herpes organisms comprising:

A. providing a specimen suspected of containing chlamydial, gonococcal or herpes organisms, B. extracting chlamydial, gonococcal or herpes antigen, respectively, from the organisms, and C. prior to or after extraction step B, contacting the specimen with a protease.

A method for the determination of a chlamydial, gonococcal or herpes antigen comprises:

A. extracting chlamydial, gonococcal or herpes antigen from a specimen suspected of containing chlamydial, gonococcal or herpes organisms, respectively, B. prior to or after the extraction in step A, contacting the specimen with a protease, C. after steps A and B, contacting the extracted antigen with antibodies thereto to form an immunological complex, and D. determining the presence of the complex as an indication of the presence of chlamydial, gonococcal or herpes organisms, respectively, in the specimen.

The extraction composition of this invention rapidly and effectively lyses chlamydial, gonococcal or herpes organisms in a biological specimen to release sufficient antigen for a sensitive assay. Thus, the present invention is an improvement in the assay described and claimed in U.S. Ser. No. 255,928 of Pronovost, Mauck, Sullivan, Greer and Gilbert (noted above) because it provides a means for effectively detecting the extracted antigen in the presence of whole blood, mucous or components thereof. In one preferred embodiment, both lipopolysaccharide and major outer membrane protein antigens of *C. trachomatis* are extracted although the lipopolysaccharide is of primary interest.

These advantages are achieved because of the use of a protease either before or after extracting the antigen using any suitable extraction procedure. The protease effectively breaks down the whole blood and mucous so that they do not interfere with the assay. Details of useful proteases are provided below.

DETAILED DESCRIPTION OF THE INVENTION

The present invention includes an extraction method, and a method for determining the presence of chlamydial, gonococcal or herpes organisms in a biological specimen which has been obtained from a patient using standard medical and microbiological techniques. Such specimens include, for example, specimens obtained from the cervix, urethra, skin, eyes, throat or anus of a patient, and body fluids such as synovial fluid or fluid from lesions. The biological specimens so obtained are suspected of containing the bacterial or viral organisms which comprise the antigens to be determined.

While some assays in the art are carried out to detect antigens from intact bacterial or viral organisms, it is usually desirable to extract the antigens from the organisms in order to increase assay sensitivity. Standard techniques can be used for lysing the organism to release antigen including, for example, solvent dilution or high pH lysing solutions, enzyme treatment and physical agitation such as sonication or centrifugation. Heating is described as a lysing technique in E.P. Publication 183,383 (published Jun. 4, 1986). The use of anionic detergents or bile salts such as sodium dodecyl sulfate and deoxycholate is described in U.S. Pat. Nos. 4,497,899, 4,497,900 and 4,663,291 (all noted above).

In a preferred embodiment, antigen detected according to the present invention is the lipopolysaccharide (glycolipid group antigen) of chlamydial organisms as described, for example, in E.P. Publication 193,431 (published Sep. 3, 1986). In addition, the major outer membrane protein of the organism may also be extracted, but the primary antigen of interest with the present invention is the lipopolysaccharide because the protease tends to break down the major outer membrane protein. This protein is described in U.S. Pat. No. 4,427,782 (noted above).

In other embodiments, various gonococcal organisms, such as *N. gonorrhoeae*, are detected by determining the presence of extracted principle outer membrane protein antigens, such as protein IA and IB, from the organisms. A single strain may be detected, or preferably, a mixture of strains are detected.

Still other embodiments represent the detection of HSV strains, either HSV-I or HSV-2 alone or both together. Glycoproteins of the virions are extracted and detected with the present invention. In addition, virally infected cells can be lysed and solubilized to release intracellular viral or membrane associated viral antigens.

Prior to or after antigen extraction, the specimen is contacted with one or more proteases. Proteases are a group of enzymes which hydrolyze the peptide bonds of proteins and form smaller peptides. They can be obtained from various sources, including microorganisms, such as bacteria and fungi, animal or human organs (for example the pancreas) plants (such as papaya) and others known in the art. Proteases can also be obtained from genetically altered microorganisms. Many proteases are commercially available (for example from Sigma Chemical Co.).

Proteases which are produced by bacteria are particularly useful in the practice of this invention. Such proteases can be classified as two general types: (1) those which are active at neutral pH and usually require a cofactor (such as zinc), called neutral proteases, and (2) those which are active at high pH and cleave peptide bonds by a process analogous to alkaline hydrolysis, called alkaline proteases. Alkaline proteases are also referred to as serine proteases which are proteolytic enzymes having a serine residue at their active site. They include chymotrypsin-like proteases and subtilisin-like proteases.

Subtilisin proteases generally act to cleave internal peptide bonds of proteins or peptides and are generally produced by various species of Bacilli (for example, *Bacillus licheniformis, Bacillus subtilis, Bacillus subtilis* strain DY and *Bacillus amyloliquefaciens*).

A preferred protease for use in this invention is described in PCT Publication 87/04461 (published Jul. 30, 1987). This protease is an analog of a *Bacillus subtilis* protease having an amino acid sequence comprising one or more Asn-Gly sequences wherein one or both amino acid residues of the sequence are deleted or are replaced by a residue of a different amino acid, such as serine or aspartic acid. It is particularly desired that the asparagine residues in positions 109 and 218 be replaced with serine residues. Further characterization and production details for these proteases are provided in the noted PCT publication, incorporated herein by reference. These preferred proteases are stable to long-term keeping.

A most preferred protease has the characteristics noted above, but in addition has one or more amino acid residues in calcium binding sites present in the amino acid sequence replaced with a negatively charged amino acid. For example, the asparagine amino acid residue in the 76 position of the sequence can be replaced by aspartic acid to great advantage in improving keeping stability. The procedures for preparing such proteases are those commonly known in the art as evidenced by the teaching in PCT Publication 87/04461 (noted above).

One highly preferred protease useful in this invention is available from the BioProducts Division of Eastman Kodak Company as Amideck ™.

The general procedure for preparation of the preferred proteases useful herein include:

1) isolation of the representative subtilisin gene aprA from *B. subtilis*, 2) cloning of the aprA gene on a vector which permits utilization of oligonucleotide site-directed mutagenesis to create desired modifications, 3) site-directed mutagenesis and sequencing of the resulting DNA to confirm the presence of the desired mutation, 4) construction of an expression vector to direct the synthesis of the mutated enzyme in *B. subtilis*, 5) construction of mutated *B. subtilis* strains which do not synthesize subtilisin and neutral protease, 6) isolation of the enzyme in the extracellular growth medium and its purification, and 7) practice of procedures for insertion of the gene coding for the improved enzyme into the chromosome of a *B. subtilis* strain previously mutated to block synthesis of endogenous proteases.

A specific preparation procedure is shown below immediately prior to the examples.

The amount of protease useful in the practice of this invention will vary depending upon the particular protease used, its source, its activity, and the amount of whole blood or mucous in the test specimen to be broken down, and other factors readily apparent to one skilled in the art. Generally, the minimal amount can be determined by the method described by DelMar et al, *Anal. Biochem.* 99, pp. 316–320 (1979). For the preferred protease identified above as Amideck ™ protease, the minimal amount useful is about 10 units/mg with from about 100 to about 1000 units/mg preferred.

The extraction method of this invention involves two separate steps:

(1) use of a protease, generally buffered to a pH of from about 7 to about 10, and (2) use of a high pH extraction composition as described herein, generally having a pH of from about 8 to about 13.5.

The protease must be kept out of a high pH environment (that is higher than about 10) or it will be inactivated. Thus, the preferred order of the steps noted above is to use the protease first. However, the steps can be reversed if the pH of the high-pH extraction composition is lowered such that the protease is not deactivated. Some antigens, for example the chlamydial major outer membrane protein, may be adversely affected by the protease. Thus, a worker skilled in the art may have to adjust the use of a protease in the method of this invention depending upon the antigen of interest.

Extraction can be carried out in any suitable container. Some extraction devices have been specifically designed for such a purpose, and a worker skilled in the art would know how to use them. U.S. Pat. No. 4,746,614 (issued May 24, 1988 to Devaney, Jr. et al) describes certain useful extraction devices.

Once the antigen is extracted from the organisms, it is desirable, although not essential, that the specimen be prefiltered to remove cell debris, particulate matter and other unwanted materials prior to further handling. Prefiltering can be carried out in any suitable container or device using known methods.

Extracted antigen can be subjected to any of a number of analytical procedures in order to determine its presence. Such procedures include culture techniques, counterimmunoelectrophoresis and serological tests which, while not preferred, may be the only choice in certain instances.

Preferably, the extracted antigen is detected using an immunoassay in which it is immunologically reacted with one or more antibodies. The resulting immunological complex is detected using a suitable radiometric, colorimetric, fluorometric or enzyme labeled reagent. In some cases, the reagent is a labeled anti-antibody directed to the antigen, and in other cases, the labeled antibody is directed to an unlabeled antibody which is reactive with the antigen. Such immunoassays generally include the formation of a detectable immunological complex on a solid support of some type, either coated or uncoated, followed by appropriate detection procedures. Other assays involve agglutination of the immunological complex when at least one reactant (such as an antibody) of the complex is attached to labeled or unlabeled particles of some type that clump together during complex formation.

Examples of useful assays include competitive immunoassays or enzyme-linked immunoabsorbent assays (or what is commonly called "ELISA"). Such assays are described generally in U.S. Pat. No. 4,427,782 (noted above) and by Schmeer et al, *J. Clin. Microbiol.*, 15(5), pp. 830–834 (1982). The chlamydial, gonococcal or herpes antibodies used can be directed to one or several antigens being extracted from the organisms. In one embodiment, antibodies are directed to a single antigen, such as the lipopolysaccharide of *C. trachomatis*. In other embodiments, a mixture of different antibodies is directed to several antigens, such as those extracted from several gonococcal strains.

A similar solid phase immunoassay is described in U.S. Pat. Nos. 4,497,899 and 4,497,900 (both noted above) in which extracted antigen is adsorbed to an uncoated support by incubation at elevated temperatures for a lengthy time.

A preferred immunoassay is described and claimed in copending U.S. Ser. No. 255,923 filed Oct. 7, 1988 by Pronovost and entitled "Determination of a Chlamydial or Gonococcal Antigen Using A Positively-Charged Ionically Binding Support". This assay is generally described as follows while further details can be obtained by consulting the noted application. The extracted antigen is contacted with a polymeric solid support which has a multiplicity of positively charged groups on the surface thereof. This support can be constructed of any natural or synthetic polymeric material with suitable cationic groups thereon which will ionically bind to the extracted antigen. Useful polymers include polyesters, polyamides, polycarbonates, polyethyleneimines, cellulosic materials, addition polymers prepared from ethylenically unsaturated vinyl monomers and others known in the art having the requisite charged groups. Generally, the cationic groups are quaternary ammonium salts, quaternary phosphonium salts, quaternary sulfonium salts, quaternary pyridinium salts, quaternary primidinium salts or quaternary imidazolium salts, with quaternary ammonium salts being preferred.

The polymeric support can be configured in any suitable form, such as beads, films, gels or membranes. The support can be coated with surfactants which may enhance assay performance. A microporous membrane is preferred as described below.

The support described herein can be used in combination with other equipment (bottles, test tubes, swabs, beakers or cups) in order carry out the assay. Alternatively and preferably, the support is a microporous membrane which is fitted into a disposable test device in which the assay can be carried out and all fluids accommodated. Useful configurations of test devices are known in the art including U.S. Pat. Nos. 3,825,410 (issued Jul. 23, 1974 to Bagshawe), 3,888,629 (issued Jun. 10, 1975 to Bagshawe), 3,970,429 (issued Jul. 20, 1976 to Updike) and 4,446,232 (issued May, 1984 to Liotta). Particularly useful devices are described and claimed in copending and commonly assigned U.S. Ser. Nos. 019,810 (filed Feb. 27, 1987 by Hinckley) and 098,248 (filed Sep. 18, 1987 by Hinckley).

In the preferred embodiments using a surfactant-coated or ionically charged support, almost immediately upon contact of the antigen with the support, the antigen is bound directly and preferentially to the support. By "directly" is meant that the antigen is not bound through a linking biological compound (such as an antibody) which is attached to the support. By "preferentially" is meant that substantially only the antigen is bound to the support, and not other materials in the reaction medium.

Therefore, within about 10 minutes, and preferably within 1 to 5 minutes, of the contact, bound antigen is contacted with either chlamydial, gonococcal or herpes antibody (depending upon the antigen) so as to form an immunological complex bound to the support. If the assay is carried out using a disposable test device, the support can be a microporous membrane through which fluid and unbound materials in the specimen are filtered as the antigen is bound to the membrane.

The chlamydial, gonococcal or herpes antibody used in this assay refers to an antibody which is specifically immunoreactive with the antigens extracted for detection in the assay. It can be polyclonal or monoclonal, may be purchased or prepared using known procedures.

In one embodiment, the antibody to the antigen is labeled for detection. Useful labels are known in the art and include chemical or biological compounds which are directly detectable using suitable procedures and equipment, as well as compounds which can be detected through further chemical or specific binding reactions to provide a detectable species. Examples of useful labels include radioisotopes, enzymes, fluorescent compounds, chemiluminescent compounds, phosphorescent compounds, biotin or its derivatives, avidin or its derivative, ferritin, magnetizable particles, dyed particles and others readily apparent to one skilled in the art. Radioisotopes or enzymes are preferred labels. The labels can be attached to antibodies using known techniques. Where the label is not directly detectable, further reagents or compounds are needed to render the reaction or specific binding product detectable. For example, if the label is biotin, it can be reacted with avidin which is conjugated with an enzyme to provide a detectable species. Where the label is an enzyme, such as glucose oxidase, urease, peroxidase, alkaline phosphatase and others, substrates and dye-providing reagents are also needed.

In a particularly preferred embodiment, the label is peroxidase, and at some point in the assay, hydrogen peroxide and suitable dye-forming reagents are added to provide a detectable dye. For example, useful dye-providing reagents include tetramethylbenzidine and derivatives thereof, and leuco dyes, such as triarylimidazole leuco dyes (as described in U.S. Pat. No. 4,089,747, issued May 16, 1978 to Bruschi), or other compounds which react to provide a dye in the presence of peroxidase and hydrogen peroxide (that is, compounds which react to provide a dye upon catalytic action of peroxidase).

In a most preferred embodiment, the chlamydial, gonococcal or herpes antibody is not labeled, and detection of the antibody-antigen complex formed and bound to the support is accomplished using a second antibody (described below) which is appropriately labeled and specific to the unlabeled antibody.

The chlamydial, gonococcal or herpes antibody can be contacted with the support-bound antigen in the presence of one or more proteins which reduce nonspecific interactions on the support. Useful proteins are well known and include, for example, casein, α-casein, fetal bovine serum and porcine gamma globulin. A particularly useful blocking composition comprises a nonimmunological protein and an amphoteric surfactant, as described and claimed in copending U.S. Ser. No. 255,925 filed Oct. 7, 1988 by Pronovost and entitled "Immunological Reagent Composition and Its Use in the Determination of Chlamydial or Gonococcal Antigens."

To hasten the formation of the immunological complex bound to the support, the antibody and antigen are generally incubated at a temperature of from about 15° to about 30° C. for up to 10 minutes. Preferably, the incubation is at room temperature (i.e. from 18° to 25° C.) for up to 5 minutes.

After the incubation and within about 10 minutes of the antibody-antigen contact, the bound complex is washed one or more times with a buffered wash solution which generally has a pH of from about 7 to about 11. The solution preferably contains one or more surfactants to aid in separating uncomplexed materials from the complex on the support. Particularly useful surfactants are cationic surfactants. Preferred wash solutions are the subject of copending U.S. Ser. No. 255,924, filed Oct. 7, 1988 by Pronovost and Gilbert and entitled "Wash Solution Containing a Cationic Surfactant and Its Use in Chlamydial and Gonococcal Assays."

In the embodiment described above where the chlamydial, gonococcal or herpes antibody is labeled, the assay procedure after washing is to detect the label directly or indirectly after addition of the appropriate reagents. This is done relatively quickly after washing the bound complex. If desired, label detection can be hastened with incubation if the reagents warrant it. The label is then detected using standard equipment and procedures.

In the preferred embodiment, the first antibody is unlabeled, and after washing the bound complex, it is contacted with a labeled antibody directed to the unlabeled antibody. This second antibody (that is an antiantibody) is appropriately labeled with any of the labels described above. The antibody can be monoclonal or polyclonal and either purchased or prepared using known techniques.

After this contact, the resulting antigen-antibody-antibody complex which is bound to the support is incubated for up to about 10 minutes at a temperature of from about 15° to about 30° C., and preferably up to about 5 minutes at room temperature (i.e. about 18° to 25° C.).

Further washing is carried out to remove uncomplexed materials, and suitable enzyme substrates or other needed reagents are added to provide a detectable species. The bound antigen-antibody-labeled antibody complex is then detected on the support using standard radiometric, colorimetric, fluorescent or other detection techniques.

The following examples are provided to illustrate, but not limit the scope of, the present invention. Materials used in Examples 1 and 2 are described as follows.

ANTIGEN PREPARATION

Serovar H antigen purified elementary bodies were obtained from Professor W. J. Newhall of Indiana University. Stock antigen solution (5 μl, containing 3240 ng antigen/μl) was added to a solution (50 μl) of bovine serum albumin in phosphate buffered saline (0.1 mg/μl) and stored at −80° C. to obtain solution A. This solution was thawed and mixed by vortexing and sonicating, followed by mixing 15 μl with the bovine serum albumin solution (945 μl) by vortexing to obtain solution B, the antigen concentration being $4.6 \times 10^5$ pg/100 μl. Solution B (100 μl) was then mixed with bovine serum albumin in phosphate buffer solution (900 μl) to obtain solution C having an antigen concentration of $4.6 \times 10^4$ pg/100 μl.

ANTIBODY PREPARATIONS

The mouse monoclonal antibody to the chlamydial lipopolysaccharide (LPS) antigen was prepared using standard hybridoma technology and a mouse cell line and stored in a solution of phosphate buffered saline solution (pH 7.4), containing 0.01 weight % sodium azide as a preservative. An antibody solution was prepared by adding a sample (19 μl) of the antibody solution to a phosphate buffered saline solution (diluting 1:800) containing casein (0.5 weight %) as a blocking protein and Lonzaine ® C amphoteric surfactant (0.01 weight %, available from Lonza Company), then filtered through a 0.22 μmeter filter to obtain a working solution.

The mouse monoclonal antibody to the chlamydial major outer membrane protein (MOMP) antigen was prepared using standard hybridoma technology and a mouse cell line and stored in a solution of phosphate buffered saline solution (pH 7.4) containing 0.01 weight % sodium azide. An antibody solution was prepared by adding a sample (14 μl) of the antibody solution to a phosphate buffered saline solution (diluting 1:1100) containing casein (0.5 weight %) as a blocking protein and Lonzaine ® C amphoteric surfactant (0.01 weight %), then filtered through a 0.22 μmeter filter to obtain a working solution.

The labeled polyclonal antibody used was a goat anti-mouse IgG antibody conjugated to horseradish peroxidase which was obtained from Bio-Rad Laboratories. This conjugate was diluted to about 1:2000 in phosphate buffered saline solution containing casein (0.5 weight %) and Lonzaine ® C amphoteric surfactant (0.01 weight %), then filtered through a 0.22 μm filter to obtain a working solution.

COMMERCIAL PROTEASE USED IN ASSAYS

The following protease enzymes were used in Examples 1 and 2, all purchased from Sigma Chemical Co. having the indicated activities (determined by the supplier):

Type XI (fungal) having an activity of 10-20 units/mg of protein,

Type IV (from *Streptomyces caespitosis*) having an activity of 0.7-1 unit/mg of solid, Type XXIV (bacterial) having an activity of 7-14 units/mg of solid, Type XXVIII (from *Tritirachium album*), having an activity of 10-20 units/mg of protein, and Type XXI (from *Streptomyces quseus*) having an activity of 15-20 units/mg of solid.

PREFERRED PROTEASE USED IN EXAMPLE 3

The Amideck ™ protease (BioProducts Division, Eastman Kodak Company) used in Example 3 was a subtilisin analog having aspartic acid in position 76, and serine in both of positions 109 and 218.

Single-stranded DNA from bacteriophage M13mp18 apr4 [$Ser^{109}$, $Ser^{218}$] (from M13mp18 bacteriophage available from Bethesda Research Laboratories, Gaithersburg, Md. catalog no. 8227SA) was annealed to a primer:

```
                     *
5' GCT CTT GAT AAC TCA ATC 3'
    74  75  76  77  78  79
    Ala Leu Asp Asn Ser Ile
``` wherein G, C, T, A, are standard symbols for the nucleotide bases, and Ala, Leu, Asp, Asn, Ser and Ile are standard abbreviations for amino acids. This primer was synthesized by the phosphite method described by Beaucage et al, *Tetrahedron Letters* 22, pp. 1859-1862 (1981). It was homologous to the nucleotides comprising codons for amino acids 74 through 79 of aprA-subtilisin except for one base change (marked by the asterisk), where adenine was changed to guanine to allow for the transition which would change $Asn^{76}$ (codon AAT) to $Asp^{76}$ (codon GAT).

The primer was annealed to M13mp18apr4 [$Ser^{109}$, $Ser^{218}$] DNA at 65° C. and the annealed DNA was slowly cooled to approximately 22° C. and then polymerized for two hours at 15° C. in a reaction mixture which consisted of 12.5 μl of annealed DNA solution, 20 μl of 10 mmolar each of dATP, dCTP and dGTP, 20 μl of 12 mmolar ATP, 0.1 μl Klenow DNA polymerase, 0.1 μl T4 DNA ligase and 13 μl sterile distilled water. The resulting double-stranded, covalently closed circular DNA was introduced into *E. coli* JM103 (available from Pharmacia Inc., Piscataway, N.J. catalog no. 27-1545-01) by transfection.

Bacteriophage plaques were transferred to hybridization membranes (such as Gene Screen ™ available from New England Nuclear, Beverly, Mass. and those which contained DNA with the desired base change were identified by hybridization to a radioactively labeled ($\gamma^{32}P$) synthetic oligonucleotide at 46° C. One positive plaque contained a bacteriophage designated as M13mp18 apr4[$Asp^{76}$, $Ser^{109}$, $Ser^{218}$]. Double-stranded DNA from the bacteriophage was digested with HindIII and KpnI in combination, then a 750 bp fragment carrying the three mutations of the aprA-subtilisin gene was ligated to the plasmid pAMB106 which had been previously digested with HindIII and KpnI. The resulting plasmid, pAMB131, was introduced into *B. subtilis* host cells for synthesis and secretion of [$Asp^{76}$, $Ser^{109}$, $Ser^{218}$]-subtilisin (that is protease).

The activity of this protease was determined using the synthetic peptide:

succinyl-L-Ala-L-Ala-L-Pro-L-Phe-p-nitroanailide (available from Sigma Chemical) as a substrate while monitoring the rate of increase in absorbance at 410 nm due to the release of p-nitroaniline. A typical reaction mixture (1 ml) contained tris(hydroxymethyl)aminomethane hydrochloride buffer (0.5 molar, pH 8), calcium chloride (1 mmolar), the peptide noted above (1 mmolar), and the protease activity was measured continuously at 25° C. Specific activity is expressed as units/mg of solid with 1 unit equivalent to a change of absorbance of 1.0 measured at 410 nm within 1 minute.

EXTRACTION COMPOSITION

An antigen extraction solution was prepared from the following components: sodium azide (0.027 molar), sodium chloride (0.27 molar), ethanolamine hydrochloride (0.47 molar), disodium ethylene-diaminetetraacetic acid (0.045 molar), Emcol TM CC-36 cationic surfactant (0.45 weight %, added from 10% solution in methanol) and sodium hydroxide (0.66 molar, pH 11.0). Emcol ® CC-36 cationic surfactant is a mixture of quaternary ammonium chlorides of polypropoxy-t-amines, available from Witco Chemical.

EXAMPLES 1 AND 2

Assays Using Protease in Extraction Composition

These examples demonstrate the advantage of using protease with the extraction composition in order to overcome the presence of whole blood in the biological specimen.

Assays were carried out using four test and control solutions and two extraction procedures. In Example 1, the extraction solution was added to the specimen followed by addition of the protease. In Example 2, the protease was added first.

In Example 1, Solution 1 contained chlamydial antigen solution C (36 µl, identified above) and whole blood (25 µl) mixed for 5 minutes at room temperature. This solution was then added to the extraction composition described above (364 µl) and incubated for 5 minutes at room temperature.

A solution of citric acid (100 µl of a 0.6 molar solution) was added to reduce the pH to about 8. The appropriate protease enzyme (400 µl of a 2 mg/ml phosphate buffered saline solution) was added and the solution was incubated for 5 minutes at room temperature. Hydrogen peroxide solution (400 µl, 10.5 weight % containing 40 µl of 10N sodium hydroxide, pH 10.5) was added and the resulting solution was incubated for 5 minutes at room temperature. It was then filtered through a 5µ Biodyne ® A membrane.

Portions (160 µl) of the above solution were added to each well of a disposable test device designed similar to that described in copending and commonly assigned U.S. Ser. No. 019,810 (noted above), and fluid was allowed to flow through immediately. The device contained a 5 µm microporous membrane having quaternary ammonium groups on the surface thereof commercially available as the Pall Biodyne ®-B membrane (Pall Corp.). Prior to use, the membrane was treated with Fluorad TM FC 135 (a fluorinated surfactant available from 3M Corp.). Each well was then washed with phosphate buffered saline solution (200 µl) containing Emcol ® CC-9 cationic surfactant (0.75 weight %).

Portions (120 µl) of a mixture (50:50) of the anti-LPS and anti-MOMP antibody solutions (prepared as described above) were added to each well of individual devices. After incubation for 5 minutes at room temperature, the resulting antigen-antibody complexes ionically bound to the membrane were washed with the wash solution described above (200 µl).

A portion (120 µl) of the peroxidase-labeled anti-antibody solution described above was added to each test well, followed by 5 minutes incubation at room temperature, and another wash.

A leuco dye composition (120 µl) was added to provide a detectable dye. This composition included hydrogen peroxide (10 mmolar), 2-(4-hydroxy-3-methoxyphenyl)-4,5-bis(4-methoxyphenyl)imidazole leuco dye (0.005 weight %), poly(vinyl pyrrolidone) (1 weight %), 4'-hydroxyacetanilide (5 mmolar) and diethylene triaminepentaacetic acid (10 mmolar). The transmission densities were then determined after another 10 minutes.

The following solutions were also assayed by the procedure described above:

Solution 2 was a control solution (no antigen) containing whole blood (25 µl) which was added to the extraction solution (375 µl) of this invention and incubated for 5 minutes at room temperature.

Solution 3 contained only antigen solution (36 µl) which was added to the extraction composition (364 µl) and incubated for 5 minutes at room temperature.

Solution 4 was a control containing only the extraction composition (400 µl).

Table I below shows the data provided in these assays for Example 1 representing the difference in transmission density between various solutions ($\Delta D_T$) and as the antigen recovery in the presence of whole blood. The data show that the use of protease improves antigen extraction in the presence of whole blood significantly, that is up to 78% depending upon the protease used.

TABLE I

| | (Example 1) $\Delta D_T$ (2000 Pg of Protein) | | |
|---|---|---|---|
| Protease Used | (Solution 3 minus Solution 4) | (Solution 1 minus Solution 2) | % Antigen Recovery |
| None | 0.182 | 0.025 | 14 |
| Type XI | 0.067 | 0.142 | 78 |
| Type XXIV | 0.101 | 0.101 | 55 |
| Type XXVIII | 0.063 | 0.106 | 58 |
| Type XXI | 0.068 | 0.068 | 37 |

Example 2 was like Example 1 except that the protease (Type XXI only, 400 µl of a 2 mg/ml phosphate buffered saline solution) was mixed with Solutions 1-4 and incubated for 5 minutes each at room temperature. The extraction composition (400 µl) was then added to each solution, followed by addition of hydrogen peroxide solution (400 µl, 9.6 weight %) and incubation for 5 minutes at room temperature. Each solution was then filtered through a 5 µm membrane (Pall Corporation).

A portion (144 µl) of each solution was then added to wells of individual test devices for attaching extracted antigen to the membrane, followed by washing with the wash solution of Example 1. The remainder of the assay was performed as described in that example.

The results of the assays are shown in Table II below. They indicate that the presence of protease enzyme improves the extraction of antigen when blood is present in the specimen.

TABLE II

(Example 2)
ΔD$_T$(2000 pg of Protein)

| Protease | (Solution 3 minus Solution 4) | (Solution 1 minus Solution 2) |
|---|---|---|
| None | 0.182 | 0.025 |
| Type XXI | 0.068 | 0.068 |

Example 3: Assay for LPS Antigen Using a Preferred Protease

This example illustrates the practice of the present invention for the determination of the lipopolysaccharide antigen of chlamydial organisms using the Amideck ™ protease, described above, which has significantly improved keeping stability.

Eighteen specimens were obtained from female patients using endocervical swabs. The specimens contained considerable whole blood or mucous or both, and had been tested for the presence of C. trachomatis using standard culture techniques.

MATERIALS USED IN THIS EXAMPLE

An extraction device like that described in U.S. Pat. No. 4,746,614 (noted above) was prepared having separate dried coatings of: (1) tris(hydroxymethyl)aminomethane buffer (from 20 μl of a 1.65 molar solution, pH 11.1) with thimerosal preservative (0.01 weight %), and (2) dithiothreitol (0.188 molar) from a 50 μl solution containing 2-(N-morpholino)ethanesulfonic acid buffer (10 mmolar), sodium azide (1.54 mmolar), ethylenediaminetetraacetic acid (5.4 mmolar) dimedone (21.4 mmolar) and poly(acrylamide) (6.35 weight %).

A protease solution was prepared having Amideck ™ protease (4 mg/ml, 170 units/mg), 2-(N-morpholino)ethanesulfonic acid buffer (10 mmolar, pH 6), sodium chloride (50 mmolar), calcium chloride (5 mmolar), 1,2-propanediol (10% w/v) and thimerosal preservative (0.01 weight %).

A hydrogen peroxide solution was prepared containing 12% (by weight) hydrogen peroxide, diethylenetriaminepentaacetic acid (10 μmolar) and thimerosal preservative (0.01 weight %).

The wash solution contained 3-cyclohexylamino-2-hydroxy-1-propanesulfonic acid buffer (pH 10.0, 0.05 molar), Emcol ™ CC-9 cationic surfactant (0.75 weight %) and preservative (0.01 weight %).

A Control reagent solution comprised anti-creatine kinase-MB antibodies (5 μg/ml), casein (0.5 weight %), Lonzaine ™ C amphoteric surfactant (0.01 weight %), preservative (0.01 weight %) in phosphate buffered saline solution (pH 7.2).

Monoclonal antibodies to the lipopolysaccharide antigen (4 μg/ml) were supplied in phosphate buffered saline solution (pH 7.2) also containing casein, Lonzaine ™ C amphoteric surfactant and preservative as noted above.

Goat anti-mouse IgG antibodies conjugated to horseradish peroxidase (conjugate available from Bio-Rad) (1:700 dilution) were supplied in phosphate buffered saline solution (pH 7.2) with casein, Lonzaine ™ amphoteric surfactant and preservative as noted above as well as 4'-hydroxyacetanilide (10 mmolar).

A leuco dye composition contained the triarylimidazole leuco dye identified in Examples 1 and 2 (0.008 weight %), poly(vinylpyrrolidone) (1 weight %), sodium phosphate buffer (pH 6.8, 10 mmolar), diethylenetriaminepentaacetic acid (10 μmolar), 4'-hydroxyacetanilide (2 mmolar) and hydrogen peroxide (10 mmolar).

ASSAY

The assay was performed as follows for each of the eighteen specimens obtained using a separate test device for each specimen. The protease solution (about 280 μl) was added to the extraction device and a patient swab was then placed therein, rotated for 5-10 seconds, followed by incubation for 3 minutes at room temperature (that is, 18°-22° C.).

The extraction solution (about 280 μl) was then added to the device containing the swab which was then rotated for another 5-10 seconds followed by incubation at room temperature for 3 minutes.

The hydrogen peroxide solution was added to the device and the same procedure was repeated.

The resulting solution in the extraction device was then removed from the device using a pipette, prefiltered and transferred to each well of a disposable test device like those described in Examples 1 and 2, adding about 160 μl to each well. One well (#1) of each test device was considered a Control well while two others (#2 and #3) were considered test wells. The vent in the device was opened allowing drainage of all fluids. Each well was then washed with the wash solution described above (160 μl) with drainage.

The Control antibody solution (about 80 μl) was added to well #1 while the anti-lipopolysaccharide antibody solution (about 80 μl) was added to each of wells #2 and #3 without drainage. Incubation at room temperature was carried out for 2 minutes.

After drainage, the wash step was repeated, and the peroxidase-labeled antibody solution (about 80 μl) was added to all wells without drainage, followed by incubation at room temperature for 5 minutes.

Following drainage and another wash step, the leuco dye composition was added to each well without drainage. After incubation at room temperature for 5 minutes, dye formation was stopped by the addition of 0.01% sodium azide solution (about 120 μl) to each well. The dye formed on the membrane of each well was observed visually and graded (0 to 10, with 0 representing no color). The results are provided in the following Table and compare the assay results to those found with the standard culture techniques. It can be seen that the assay was highly accurate, determining all negative specimens and 83% of the positive specimens.

TABLE

| Specimen | Culture Results | Visual Readings | | | Assay +/− |
|---|---|---|---|---|---|
| | | Control | Well #2 | Well #3 | |
| 1 | Positive | 2-3 | 4 | 4 | Positive |
| 2 | Negative | 1-2 | 1-2 | 1-2 | Negative |
| 3 | Negative | 2 | 2 | 2 | Negative |
| 4 | Negative | 1 | 1 | 0-1 | Negative |
| 5 | Positive | 1 | 10 | 10 | Positive |
| 6 | Negative | 1-2 | 0-1 | 0-1 | Negative |
| 7 | Positive | 1 | 10 | 10 | Positive |
| 8 | Negative | 2-3 | 2 | 2 | Negative |
| 9 | Positive | 1 | 6 | 6 | Positive |
| 10 | Positive | 1-2 | 5 | 5 | Positive |
| 11 | Positive | 1-2 | 1 | 1 | Negative |
| 12 | Positive | 6 | 7 | 7 | * |
| 13 | Positive | 1 | 5-6 | 5-6 | Positive |
| 14 | Positive | 1 | 7-8 | 7-8 | Positive |
| 15 | Positive | 1 | 10 | 10 | Positive |
| 16 | Positive | 1 | 9 | 9 | Positive |
| 17 | Positive | 1 | 5-6 | 5-6 | Positive |

TABLE-continued

| Specimen | Culture Results | Visual Readings | | | Assay +/− |
|---|---|---|---|---|---|
| | | Control | Well #2 | Well #3 | |
| 1* | Positive | 1 | 1 | 0-1 | Negative |

*No test, that is, assay procedure was done incorrectly.

The invention has been described in detail with particular reference to preferred embodiments thereof, but it will be understood that variations and modifications can be effected within the spirit and scope of the invention.

We claim:

1. A method for providing extracted antigen from chlamydial, gonococcal or herpes organisms comprising:
   A. providing a specimen suspected of containing chlamydial, gonococcal or herpes organisms,
   B. extracting chlamydial, gonococcal or herpes antigen from said organism to provide extracted antigen in said specimen, and
   C. prior to or after step B, contacting said specimen with a protease which is an analog of a *Bacillus subtilisin* having an amino acid sequence comprising an Asn-Gly sequence wherein one or both amino acid residues of said sequence are deleted or replaced by a residue of serine or aspartic acid,
   provided that when said specimen is contacted with said protease after antigen extraction in step B, the antigen provided is predominantly a lipopolysaccharide,
   further provided that said method is carried out in less than about 15 minutes.

2. The method of claim 1 wherein said extraction step B is carried out at room temperature for up to about 10 minutes using an extraction composition.

3. The method of claim 1 carried out in an extraction device.

4. The method of claim 1 wherein extraction step B is carried out at a pH of from about 8 to about 13.5.

5. The method of claim 1 wherein said Asn residue of said sequence is replaced with a serine residue in the 109 and 218 positions.

6. The method of claim 5 wherein said protease has the Asn residue in the 76 position replaced with aspartic acid residue.

7. A method for the determination of a chlamydial, gonococcal or herpes antigen comprising:
   A. providing extracted chlamydial, gonococcal or herpes antigen from a specimen suspected of containing chlamydial, gonococcal or herpes organisms, respectively,
   B. prior to or after the antigen extraction of step A, contacting the specimen with a protease which is an analog of a *Bacillus subtilisin* having an amino acid sequence comprising an Asn-Gly sequence wherein one or both amino acid residues of said sequence are deleted or replaced by a residue of serine or aspartic acid,
   provided that when said speciment is contacted with said protease after antigen extraction, the antigen so provided is predominantly a lipopolysaccharide,
   C. after steps A and B, contacting said extracted antigen with antibodies thereto to form an immunological complex, said complex being bound to a microporous membrane, and
   D. determining the presence of said complex on said membrane as an indication of the presence of chlamydial, gonococcal or herpes organisms, respectively, in said specimen,
   provided that said method is carried out within about 35 minutes at a temperature of from about 15° to about 30° C.

8. The method of claim 7 wherein step B precedes step A.

9. The method of claim 7 wherein said protease has Ser residues in the 109 and 218 positions and Asp in the 76 position of said amino acid sequence.

10. The method of claim 7 wherein said chlamydial, gonococcal or herpes antibodies are labeled for detection.

11. The method of claim 10 wherein said label is an enzyme.

12. The method of claim 7 wherein said chlamydial, gonococcal or herpes antibodies are unlabeled, and said immunological complex is detected using labeled antibodies to the unlabeled antibodies.

13. The method of claim 7 for the detection of *C. trachomatis* organisms by extraction and detection of predominantly the lipopolysaccharide antigen.

14. The method of claim 7 for the detection of *N. gonorrhoeae* by extraction and detection of predominantly the protein IA or IB antigen.

15. The method of claim 7 wherein said solid support is a microporous membrane in a disposable test device.

* * * * *